United States Patent [19]

Sakamaki

[11] Patent Number: 4,908,186
[45] Date of Patent: Mar. 13, 1990

[54] AUTOMATED CHEMICAL ANALYZER
[75] Inventor: Takeshi Sakamaki, Tokyo, Japan
[73] Assignee: Kabushiki Kaisha Toshiba, Kawasaki, Japan
[21] Appl. No.: 904,644
[22] Filed: Sep. 8, 1986
[30] Foreign Application Priority Data
  Sep. 11, 1985 [JP] Japan ................. 60-199526
[51] Int. Cl.⁴ .................................. G01N 35/04
[52] U.S. Cl. .......................... 422/64; 422/67; 436/47
[58] Field of Search ............ 422/64, 67, 72; 436/45, 436/43, 47

[56] References Cited
U.S. PATENT DOCUMENTS

| | | | |
|---|---|---|---|
| 4,227,886 | 10/1980 | Bullock et al. | 422/64 X |
| 4,263,256 | 4/1981 | Morle | 422/61 X |
| 4,313,735 | 2/1982 | Yamashita et al. | 422/64 X |
| 4,325,910 | 4/1982 | Jordan | 422/64 |
| 4,457,893 | 7/1984 | Takekawa | 422/64 |
| 4,664,885 | 5/1987 | Minekane | 422/65 |
| 4,690,900 | 9/1987 | Kimmo et al. | 122/67 X |
| 4,699,766 | 10/1987 | Yamashita | 422/64 |
| 4,781,891 | 11/1988 | Galle | 422/65 |

Primary Examiner—Michael S. Marcus
Attorney, Agent, or Firm—Finnegan, Henderson, Farabow, Garrett and Dunner

[57] ABSTRACT

Two turntables are arranged in a concentric array with a plurality of reaction tubes arranged on each respective turntable, in which one turntable is rotated while, on the other hand, the other turntable is stopped. It is possible to measure the intensity of a light beam passed through the reaction liquid within the reaction tube on the turntable being rotated. The pouring of a sample, pouring of a reagent and washing/drying are achieved with respect to the reaction tubes on the turntable being stopped. The pouring of the sample and reagent and washing of the tubes are achieved parallel with the extraction of the measured data, thus assuring a shorter analytical handling time.

9 Claims, 7 Drawing Sheets

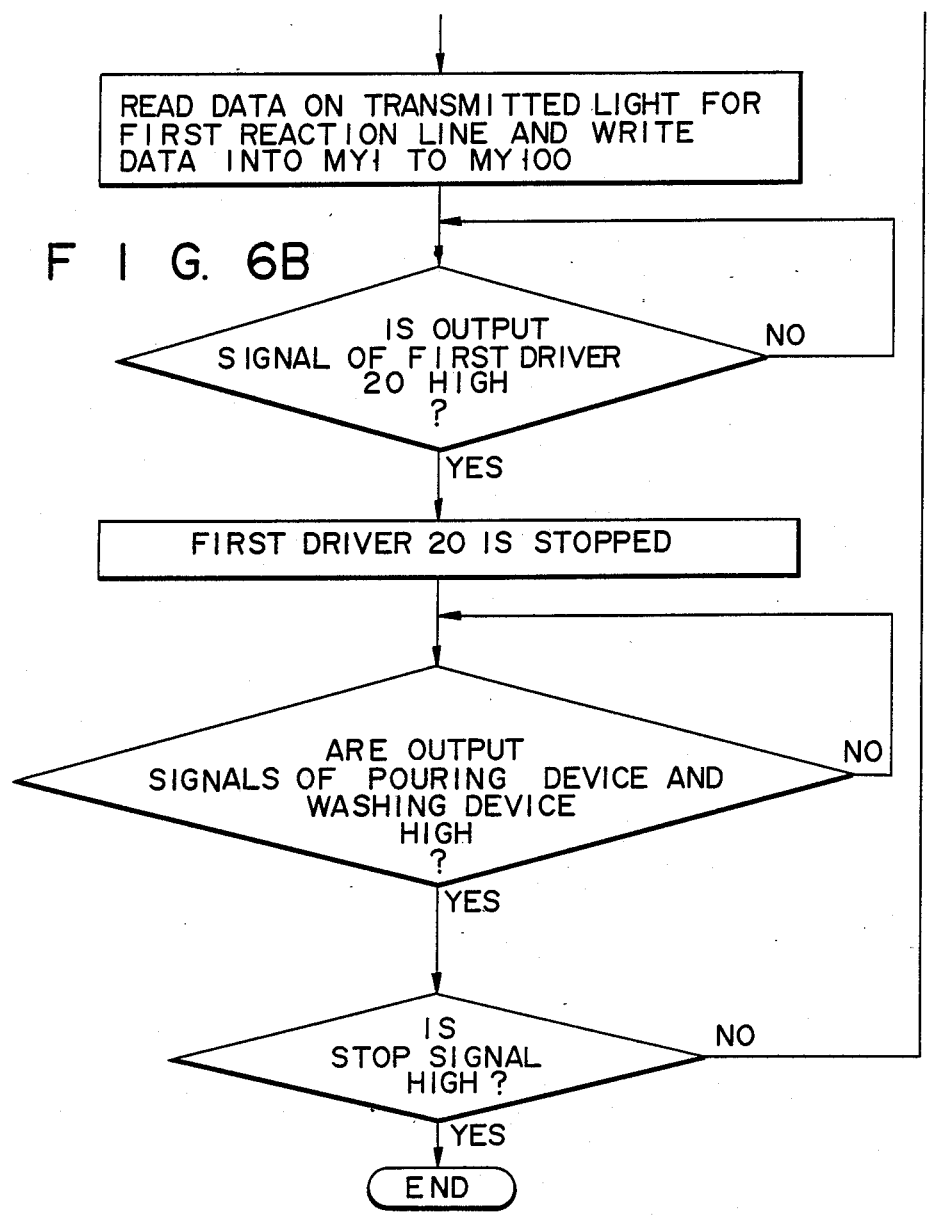

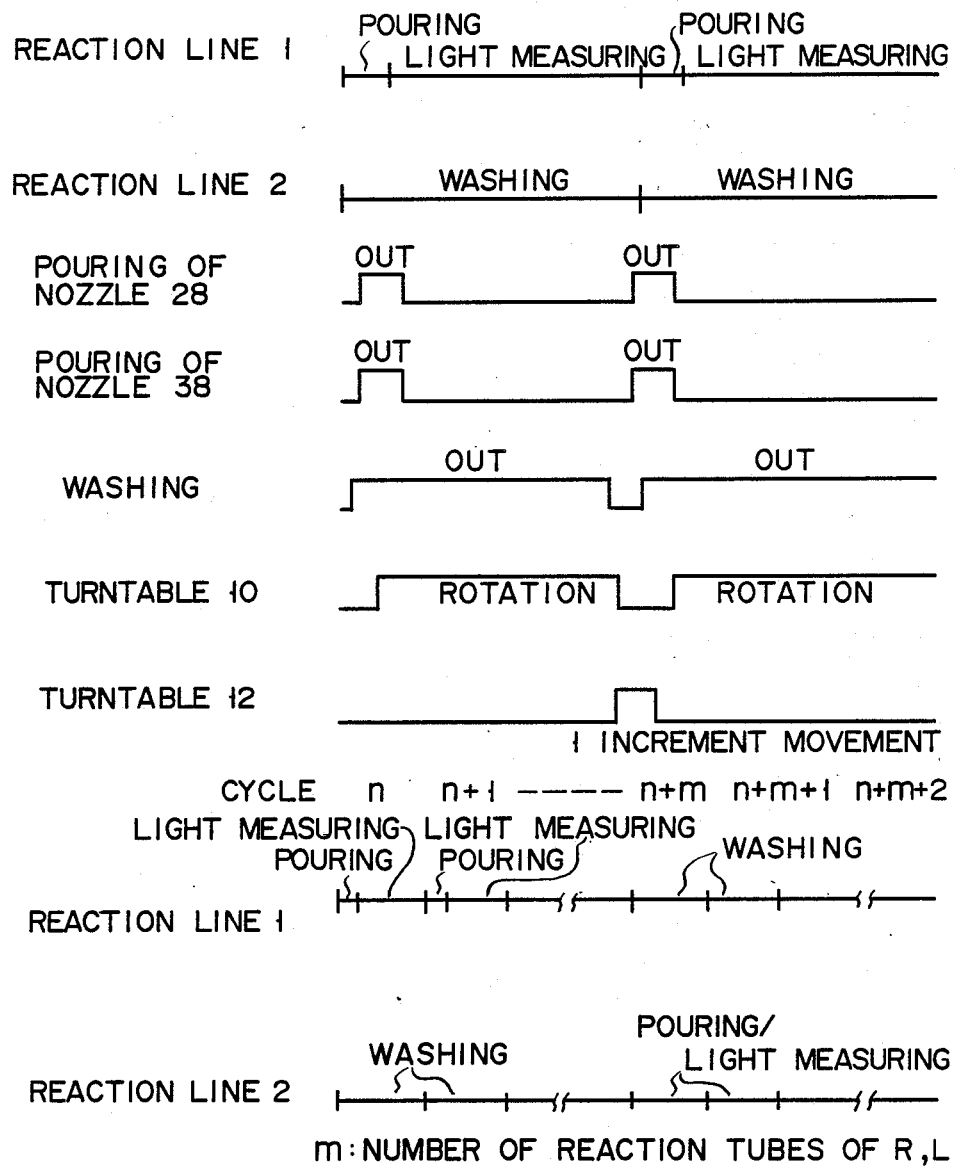

AUTOMATED CHEMICAL ANALYZER

BACKGROUND OF THE INVENTION

This invention relates to a high-speed automated chemical analyzer suited to clinical examination.

Recently, as an important clinical technique, attention has been focused on diagnosing disease through the utilization of the decomposition of enzyme components in blood. In the case of hepatic diseases, for example, the hepatic function is checked based on the measurement of enzymes released from the cells of the liver into blood, such as a gultaric/oxaloacetic acid transamylase (hereinafter referred to GOT), gultaric/pyruvic transamylase (hereinafter referred to as GPT) and $\gamma$-glutamyl-transpeptidase (hereinafter referred to as $\gamma$-GTP)

The IFCC has correctly recommended that the medical analyst examine not only the concentration level but also the activity level of enzymes. The activity level of the enzyme is expressed in a given unit and one unit of the enzyme is defined as an amount of enzyme required to vary 1 $\mu$ mol of the substrate per minute under a proper condition.

As a means for measuring the activity level of the enzyme, an ultraviolet portion reaction rate method (hereinafter referred to as a rate method) is generally known, which mixes with a blood serum a reagent containing the coenzyme nicotineamideadeninenucleoside (hereinafter referred to as $NADH_2$) to oxidize $NADH_2$ and time-sequentially monitors a variation in light absorption resulting from the oxidation process, whereby that activity level is evaluated.

The activity level of the enzyme in blood serum is extremely low and GOT in a healthy man is in the order of 10 to 30 IU/ml, noting that IU is an international unit. A change in absorbance of $NADH_2$ in 340 nm corresponding to this activity level is about 0.001 to 0.003 (AbS). In order to measure the enzyme with high accuracy, a monitoring of over 1 minute will be necessary due to a smaller change in that absorbance. In this case, a discrete type one-channel automated chemical analyzer can handle only less than 60 samples per hour for checking.

In order to measure the activation level of the enzyme with high accuracy it will be necessary to confirm the linear progress of reaction, while monitoring its reaction state. It is preferred that the reaction be monitored at least for a few minutes.

Recently it is desired that in clinical examination a greater number of samples be checked for a brief period of time for the acquisition of data on a greater number of items for checking.

A large-sized automated chemical analyzer is known in the art which handles a greater number of samples over a greater number of data items on multichannel reaction lines. In this machine, however, data items to be checked are restricted for each reaction line and, moreover, it is necessary to transfer a reaction liquid from a reaction container to a cell for light measurement so that a light beam passed through the reaction liquid within the reaction container may be measured for evaluation. For a measurement to be made with high accuracy, however, a longer time is required and thus it is not possible to analytically handle samples at high speeds.

Another automated chemical analyzer is known in the art which can handle a number of data on samples in one channel. In this machine, a turntable is rotated with a number of reaction tubes arranged along a reaction line on the outer periphery thereof and, while this is done, the reaction liquid within the respective tube is directly observed. In this case, the observation of the reaction tubes is repeated, for a predetermined period of time, from the initiation to the termination of the reaction. Since only a short observation time is required for each reaction tube, it is possible to rapidly handle data items on samples, while maintaining a high measuring accuracy.

In this machine, however, it would be difficult to handle a greater number of samples in one reaction line and, for a greater amount of data items to be handled, a few sets of reaction bath blocks should be assembled for the peripheral reaction line, resulting in a bulkier machine.

SUMMARY OF THE INVENTION

It is accordingly the object of this invention to provide a compact, automated chemical analyzer which can analytically handle a greater number of samples with high speeds and high accuracy.

According to this invention, an automated chemical analyzer is provided which comprises:

a plurality of turntables having circumferential reaction lines arranged in a concentric relation;

driving means for rotationally driving the respective turntables;

a plurality of reaction receptacles mounted on the turntable along the respective reaction line;

light measuring means for measuring an amount of light beam passed through a reaction liquid within the reaction receptacle;

sample pouring means for pouring a sample into the reaction receptacle;

reagent pouring means for pouring a reagent into the reaction receptacle;

washing/drying means for washing and drying the reaction receptacle; and control means for measuring, while rotationally driving at least one turntable by the driving means, the light beam from the reaction liquid within the reaction receptacle supported on the turntable being rotated, and for driving at least one of the sample pouring means, reagent pouring means and washing/drying means with respect to the reaction receptacle supported on the turntable being stopped.

According to this invention, an automated chemical analyzer is provided which evaluates a change in amount of decomposed enzyme by measuring, while rotating at least one turntable, an amount of light beam passed through a reaction liquid within a respective reaction receptacle on the turntable each time the respective reaction receptacle intersects a spot set for a light measuring means. While, on the other hand, another turntable is stopped, a sample is poured into emptied reaction receptacles on that turntable, a reagent is poured into sample-contained receptacles to cause the sample to react with the reagent and after the completion of the reaction and the measurement the reaction liquid is discharged from the reaction liquid-contained receptacles for washing.

According to this invention, it is possible to shorten the processing time for checking, because the pouring of a sample or reagent, measurement of the light beam passed through the reacted liquid within the reaction receptacle and washing of the reaction receptacle are concurrently effected in a parallel fashion. By alternately repeating the light measuring and injection/washing steps it is possible to monitor the reaction state of the reaction liquid in a time-sequential fashion and thus to measure the activation level of the enzyme with high accuracy. Furthermore, a greater number of samples can be measured on a compact machine because of a shorter processing time per reaction container.

BRIEF DESCRIPTION OF THE DRAWINGS

FIGS. 6A and 6B each show a flowchart for showing the operation of a controller (100) in FIG. 1;

FIGS. 8 and 9, each, are a timing chart showing a controller in a automated chemical analyzer according to another embodiment of this invention.

DETAILED DESCRIPTION OF THE PREFERRED EMBODIMENT

Figure 1:
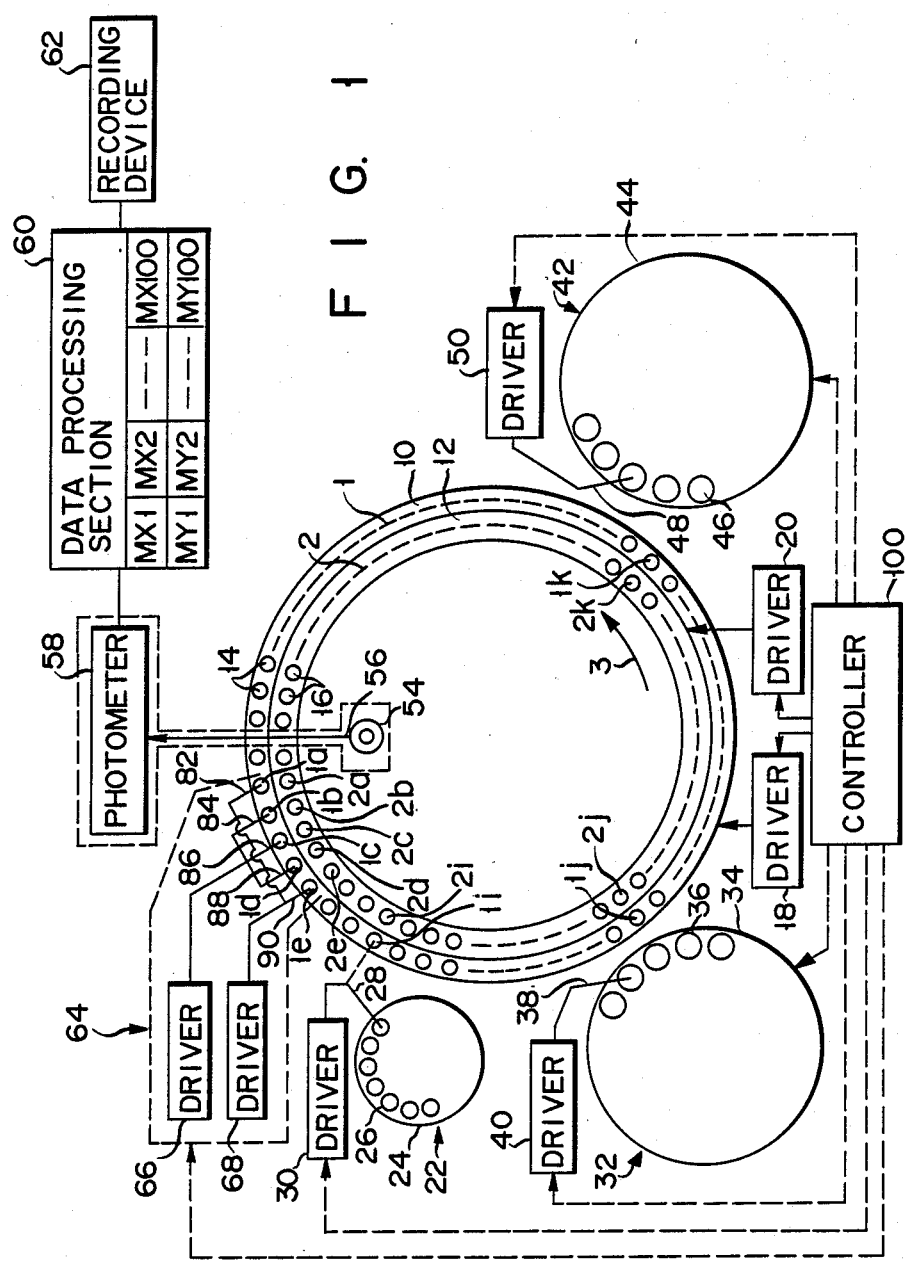
FIG. 1 is a view showing an automated chemical analyzer according to this invention.

FIG. 1 is a block diagram illustrating a model in a view for showing a control system for an automated chemical analyzer according to an embodiment of this invention. Ring-like turntables 10 and 12 are concentrically arranged such that turntable 10 is located as an outer turntable with respect to inner turntable 12. Reaction tubes 14 and 16 are placed in arrays on outer and inner turntables 10 and 12, respectively, and arranged along reaction lines 1 and 2, respectively. Turntables 10 and 12 can be rotated around their center independently of each other as indicated by an arrow 3 in FIG. 1 with their reaction tubes supported thereon. Respective drivers 18 and 20 rotate turntables 10 and 12 at a pitch of 360°+1 increment upon receipt of a drive signal from controller 100, provided that the increment +1 corresponds to a distance of reaction tubes 14 and 16 in the arrays, that is, on angle corresponding to a distance between the reaction tubes. For 100 reaction tubes in one reaction line, for example, that increment +1 is equal to 3.6°. Respective drivers 18 and 20 deliver high-level output signals to controller 100 when turntables 10 and 12 are stopped.

Figure 2:
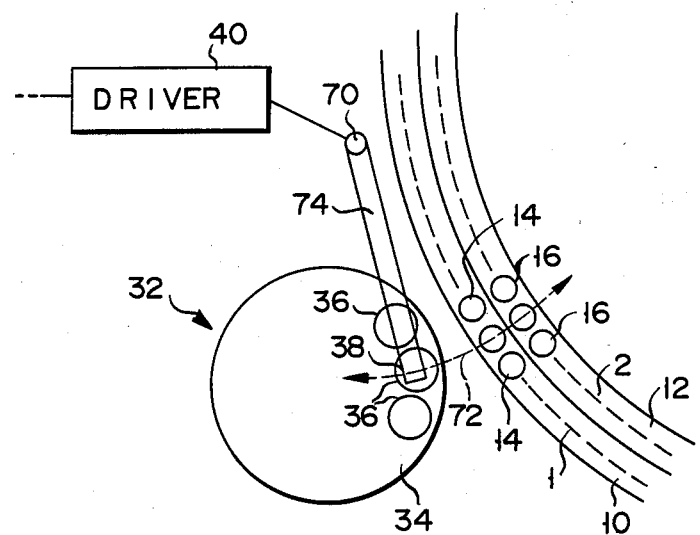
FIG. 2 is an expanded view showing a detail of a reagent pouring device (32) in FIG. 1.

Sample pouring device 22, first reagent pouring device 32, second reagent pouring device 42, light measuring device 52 and washing device 64 are arranged in that order along the rotation direction of turntables 10 and 12 as indicated by an arrow 3 in FIG. 1. In reagent pouring device 32 as shown expanded in FIG. 2, disk-like turntable 34 is rotatably mounted with its rotation axis as a center and a plurality of first reagent receptacles 36 containing reagents of first type are placed around the outer peripheral portion of turntable 34. Arm 74 is swung around fulcrum 70 and, when nozzle 38 attached to the distal end of arm 74 is swung along locus 72, it can be located immediately above the corresponding reaction tube (1j, 2j) arranged on the reaction line (1, 2). When nozzle driver 40 receives an pouring start signal from controller 100, it rotates turntable 34 to allow reagent receptacle 36 containing a predetermined reagent to be selected and then operates arm 74 and nozzle 38 to allow the reagent to be sucked from receptacle 36 and poured into reaction tube 1j when turntable 10 is stopped, and into reaction tube 2j when turntable 12 is stopped. Upon the completion of the reagent pouring, nozzle driver 40 delivers a high-level output signal (injection completion signal) to controller 100.

Sample pouring device 22 includes turntable 24, sample receptacles 26, nozzle 28 and nozzle driver 30 and second reagent pouring device 42 includes turntable 44, sample receptacles 46, nozzle 48 and nozzle driver 50. The detail of these devices 22 and 42 is substantially the same as that of first reagent pouring device Thus further explanation of them is omitted.

Figure 3:
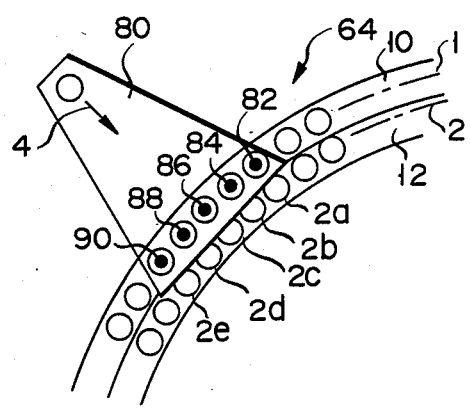
FIG. 3 is an expanded view showing a detail of a washing device in FIG. 1.

Washing device 64 washes reaction tubes 1a, . . . -and 1e when turntable 10 is stopped and reaction tubes 2a, . . . - and 2e when turntable 12 is stopped. As shown in FIG. 3, nozzle station 80 is supported by a proper support means such that it is moved to and from turntables 10 and 12 as indicated by an arrow 4 in FIG. 3. Five nozzles 82, 84, 86, 88 and 90 are attached to the forward end portion of nozzle station 80, noting that nozzles 82 and 90 are used for discharging (sucking of reaction liquid or washing liquid) only and driven by washing-/discharge driver 68.

Figure 4:
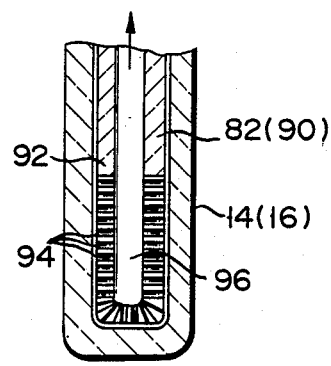
FIG. 4 is a longitudinal view showing a discharge-only nozzle in FIG. 1.

Discharge-only nozzles 82 and 90 have bottomed cylinder 92 each with a greater number of suction holes, as shown in FIG. 4. Interior 96 of cylinder 92 connected to a proper suction pump, not shown. Reaction tube 14 (or 16) is inserted into nozzle 82 (or 90) to allow a reaction liquid or washing liquid within reaction tubes 14 and 16 to be discharge through the vacuum suction of the interior (96) of cylinder 92 with cylinder 92 placed in intimate contact with the inner surface of the reaction tube. Wash nozzles 84, 86 and 88 may be used for injecting washing liquid into the reaction tube and also for sucking washing liquid from the reaction tube by virtue of drivers 66. When drivers 66 and 68 receive an operation start signal from controller 100, nozzle station 80 is advanced in such a direction that nozzles 82 to 90 are located just above the corresponding reaction tubes on turntables 10 and 12 when stopped. Upon the drive of nozzle 82, the reaction liquid of corresponding reaction tube 1a or 2a is discharged (sucked); upon the drive of nozzles 84 to 88 the washing liquid of the corresponding tube (1b to 1d) or (2b to 2d) is injected and sucked a few items; and upon the drive of nozzle 90 the washing liquid left within the corresponding reaction tube 1e or 2e is sucked for discharge and drying. Upon the completion of a washing/drying operation by the nozzles, a high-level output signal is delivered to controller 100.

It is to be noted that the distance between the reaction tubes on the reaction line and that between the reaction tubes on the other line vary due to a difference in the curvatures of the reaction lines and thus the center of respective nozzles 82 to 90 is completely not aligned with that of reaction tubes 1a to 1e or 2a to 2e. In spite of such a misalignment, nozzles 82 to 90 are loosely attached to nozzle station 80, so they can smoothly been inserted into the corresponding reaction tube.

Figure 5:
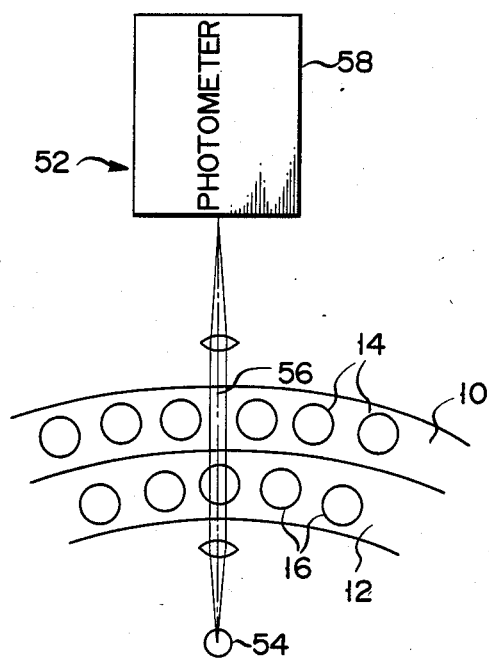
FIG. 5 is a view showing a portion of a light measuring device in proximity to a reaction line in FIG. 1.

Light measuring device 52 has light source 54 located inside reaction lines 1 and 2 and photometer 58 located on optical path 56 from the light source. As shown in FIG. 5, when turntable 10 for reaction line 1 is stopped, a light beam passes between reaction tubes 14, and during the rotation of turntable 12, reaction tubes 16 on the turntable 12 intersect with the optical path, the beam passes into the reaction liquid (within the corresponding reaction tube 16), so that photometer 58 measures the intensity of that transmission light beam. The measured value of photometer 58 is input to data processing section 60 where it is stored. For example, where 100 reaction tubes (14, 16) are provided for the respective reaction line (1, 2) data processing section 60, upon receipt of a light measuring start signal from controller 100, measures, at each passage of reaction tubes 14 or 16 across optical path 56, the intensity of the light beam which has been transmitted through the reaction liquid, so that a predetermined number (100, for example) of data can be input to data processing section 60 where the data are stored in memories MX1 to MX100 or MY1 to MY100. Upon the completion of a series of measuring operations, data processing section 60 arranges data in these memories for the respective reaction tubes and recognizes these data as time-sequential data for the respective reaction liquids. From the measured data, data processing section 60 calculates the activity level of an enzyme and records it onto recording device 62.

Figure 6A:
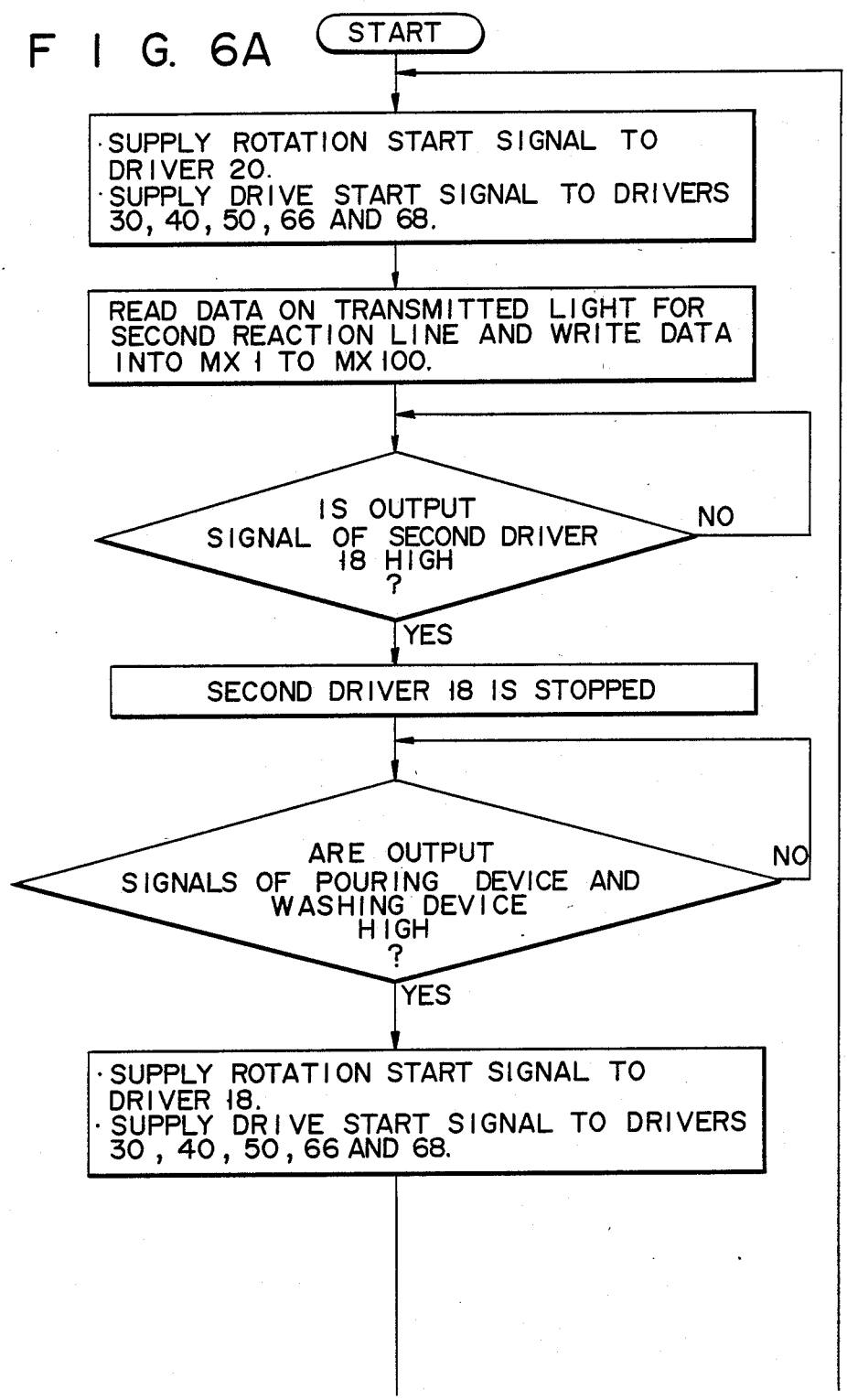
Figure 7:
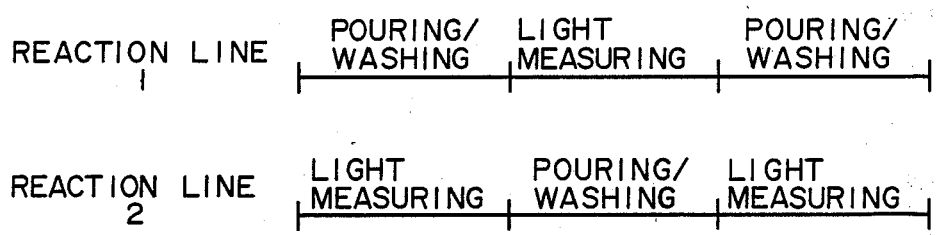
FIG. 7 is a timing chart showing the operation of the controller in FIG. 1.

The operation of the automated chemical analysis so configured will be explained below with reference to the flow chart of FIGS. 6A and 6B and operation timing chart of FIG. 7.

Controller 100 delivers an output signal as a rotation start signal to second driver 20 for driving turntable 12 and an output signal as a drive start signal to nozzle drivers 30, 40, 50, 66 and 68. By so doing, turntable 12 starts to be rotated to allow the intensity of the light beam which has been transmitted (while on the optical path, through the reaction liquid in reaction tube 16) to be detected by virtue of photometer 58. During the rotation of turntable 12, data processing section 60 accepts, for example, 100 data items on the intensity of the transmitted light beams and allows them to be stored in memories MX1 to MX100. When turntable 12 is rotated at a pitch of 360°+1 increment, driver 20 stops turntable 12 and delivers a high-level signal to controller 100. By such a rotation, respective reaction tube 16 is moved in the direction of arrow 3 to a "one increment ahead" position. Thus, the reaction tube, with its liquid discharged by nozzle 82 during the previous stopping of the turntable, is stopped, for each rotation of the turntable, at the position of nozzle 84 and washed by that nozzle. During the stopping of turntable 10, on the other hand, sample pouring device 22, first reagent pouring device 32, second reagent pouring device 42 and washing device 64 are operated. Nozzle 28 sucks the sample from predetermined sample receptacle 26, which has been selected by the rotation of turntable 24, and pours it into reaction tube 1i. Nozzle 38 sucks the reagent from predetermined reagent receptacle 36, which has been selected by the rotation of turntable 34, and pours it into reaction tube 1j. As required, the reagent within reagent receptacle 46 is poured into reaction tube 1k from nozzle 48 of second reagent pouring device 42. It is to be noted that nozzles 28, 38 and 48 are washed at their respective washing stations in devices 22, 32 and 42 for preventing the samples and reagents from being carried over. The reaction liquid within reaction tube 1a is sucked and discharged by nozzle 82. Reaction tubes 1b to 1d are injected and discharged with washing liquid a few times by nozzles 84 to 88. The washing liquid left within reaction tube 1e is discharged through nozzle 90. Upon the completion of pouring and washing operations respective drivers 30, 40, 50, 66 and 68 deliver high-level output signals to controller 100.

Upon the completion of the pouring and washing operations, controller 100 delivers start signal to first driver 18 for rotating turntable 10, and the light measurement of reaction tubes 14 for reaction line 1, as well as the pouring and washing of reaction tubes 16 for reaction line 2, is performed in a similar way. Controller 100 performs these operations repeatedly until controller 100 receives a stop signal to allow the data on the intensities of a requisite number of transmitted light beams to be stored in data processing section 60. Data processing section 60 calculates the activity levels of the liquids of the respective reaction tubes on the basis of the respective data and stores them in recording device 62.

About 5 to 6 seconds are required for every 100 reaction tubes so as to gain the corresponding measured data. It takes about 5 to 6 seconds to complete the washing and drying operations for the reaction tubes. For this reason, it is only necessary to perform the rotation and stopping operations of the turntable every 5 to 6 seconds. In this embodiment of this invention the light measuring and pouring/washing operations are performed concurrently, making it possible to effect an analytical processing at a handling speed 2 times as high as that of the conventional chemical analyzer for a one reaction line type.

Figure 8:
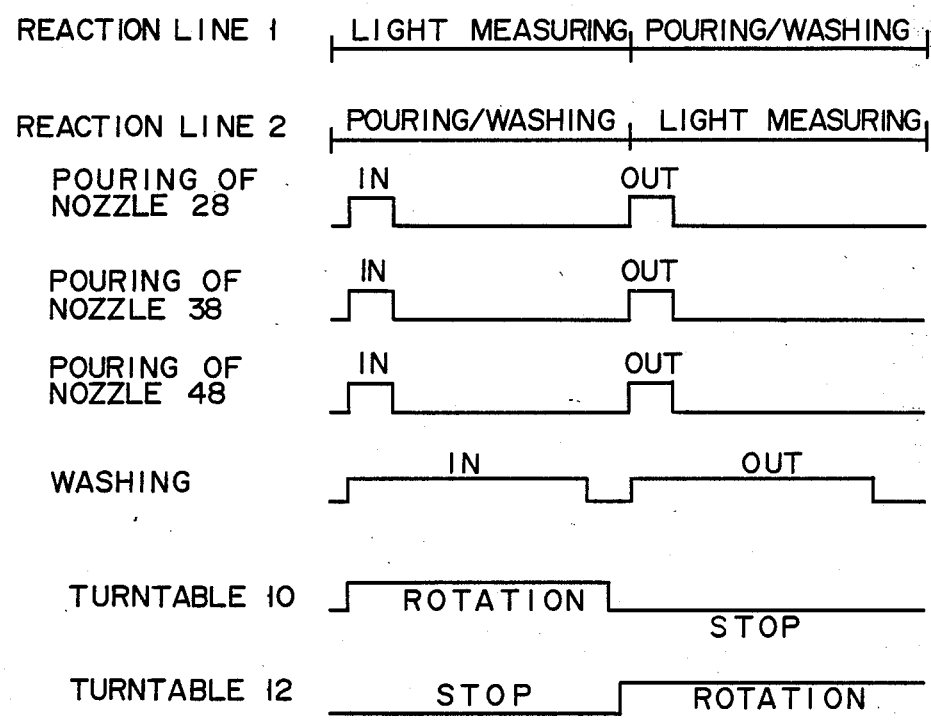

In the aforementioned embodiment, the light measuring and pouring/washing operations for reaction line 1 and those for reaction line 2 are alternately repeated. However, this invention is not restricted thereto and various proper operations can be performed according to this invention. As shown in the timing chart of FIG. 8, for example, the light measuring and pouring/washing operations can be switched after such operations have been effected a plurality of times. As shown in the timing chart of FIG. 9, it is possible to repeat pouring and light measuring operations for reaction line 1, while continuing the washing operation.

Although, in the aforementioned embodiments, for example, the inside and outside turntables have been explained as being driven at the same cycle, these may be done at a different cycle, with one of them set in an integral multiple relation to the other. In this case this invention can be used for an application where two types of reaction speeds are involved on a single machine. That is, one turntable performs a stopping/rotation operation once for one line, while, on the other hand, the other turntable performs a stopping/rotation operation twice for the other line, in which case the reaction times can be selected with the use of shorter and longer lines.

In the aforementioned embodiment, where the turntables are alternately driven in a concentric fashion, it is possible to attain a handling speed 2 times as high as that on a many-items-per-line handling machine.

If turntables are driven, in independent cycles, for a double reaction line with one cycle set in an integral multiple relation to the other cycle, an automated chemical analyzer which is broader in application can be provided, in which the turntables are driven on a single machine with different reaction times.

In the aforementioned embodiment, drivers 18 and 20 rotate turntables 10 and 12 at a pitch of 360°+1 increment upon receipt of a drive signal from controller 100. However, drivers 18 and 20 may rotate turntables 10 and 12 at a pitch of $(360/n)°+1$ increment upon receipt of the drive signal, where n is a natural number.

What is claimed is:

1. An automated chemical analyzer comprising:
   a plurality of turntables concentrically arranged, each of said turntables having a circumferential reaction line including a plurality of reaction receptacles disposed coangularly with an interval therebetween;
   driving means for rotating each of said turntables independently;
   light source means for emitting a light beam passing through a reaction receptacle disposed on a reaction line of one of said turntables and passing through the interval or intervals disposed on the reaction line or lines of said remaining turntables; and
   light-measuring measuring means for measuring said light beam, said reaction lines of said turntables disposed between said light source means and said light-measuring means.

2. The automated chemical analyzer according to claim 1, wherein at least one of said turntables is annular, said driving means is capable of rotating at least one of said turntables while stopping one or more of the remaining turntables, said reaction receptacles contain a reaction liquid, said light source means emits said light beam toward said reaction liquid contained in each reaction receptacle supported by any turntable that is rotating, and said light-measuring means measures the amount of light passing through said reaction liquid contained in each reaction receptacle supported by any turntable that is rotating.

3. The automated chemical analyzer according to claim 2 further comprising:
   sample-pouring means for pouring a sample into each reaction receptacle supported by any turntable that has been stopped;
   reagent-pouring means for pouring a reagent into each reaction receptacle supported by any turntable that has been stopped;
   washing/drying means for washing and drying each reaction receptacle supported by any turntable that has been stopped; and
   control means for controlling said light-measuring means, said sample-pouring means, said reagent-pouring means, and said washing/drying means, thereby causing said light-measuring means to perform its function on said reaction receptacles supported by said turntable being rotated, while causing at least one of said sample-pouring means, reagent pouring means, and washing/drying means to perform their functions on said reaction receptacles supported by the turntable or turntables which have been stopped.

4. The automated chemical analyzer according to claim 3, in which said driving means rotates said one or more turntables at a pitch of $360° + 1$ increment corresponding to the predetermined angular interval between adjacent reaction receptacles supported by the said one or more turntables which are rotating.

5. The automated chemical analyzer according to claim 3, in which said driving means rotates said one or more turntables at a pitch of $(360/n)° + 1$ increment corresponding to the predetermined angular interval between adjacent reaction receptacles supported by said one or more turntables which are rotating.

6. The automated chemical analyzer according to claim 3, wherein said plurality of turntables comprises a first turntable, a second turntable, a first reaction line on said first turntable, and a second reaction line on said second turntable.

7. The automated chemical analyzer according to claim 6, in which said driving means has a means for rotating said first turntable while stopping said second turntable, and vice versa.

8. The automated chemical analyzer according to claim 6, in which said driving means has a means for rotating said first turntable a number of times while stopping said second turntable, and vice versa.

9. The automated chemical analyzer according to claim 6, in which said driving means has a means for rotating said first turntable one time while stopping said second turntable, and then rotating said second turntable a number of times while stopping said first turntable.

* * * * *